(12) United States Patent
Miyashita et al.

(10) Patent No.: US 7,323,098 B2
(45) Date of Patent: Jan. 29, 2008

(54) BIOSENSOR AND MEASURING METHOD USING THE SAME

(75) Inventors: Mariko Miyashita, Nishinomiya (JP); Toshihiko Yoshioka, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 799 days.

(21) Appl. No.: 10/653,257

(22) Filed: Sep. 3, 2003

(65) Prior Publication Data
US 2004/0040866 A1 Mar. 4, 2004

(30) Foreign Application Priority Data
Sep. 3, 2002 (JP) ............................. 2002-257647

(51) Int. Cl.
*G01N 27/327* (2006.01)
(52) U.S. Cl. .............................. 205/777.5; 204/403.03; 204/403.04
(58) Field of Classification Search ................. 204/403.01–403.15, 409–412; 205/777.5, 205/778, 792
See application file for complete search history.

(56) References Cited

U.S. PATENT DOCUMENTS

| | | | |
|---|---|---|---|
| 5,120,420 A | | 6/1992 | Nankai et al. |
| 5,264,103 A | | 11/1993 | Yoshioka et al. |
| 5,395,504 A | | 3/1995 | Saurer et al. |
| 6,855,243 B2 * | | 2/2005 | Khan .................. 205/777.5 |

FOREIGN PATENT DOCUMENTS

| | | | |
|---|---|---|---|
| JP | 4-284246 A | | 9/1992 |
| JP | 5-196596 | | 8/1993 |
| JP | 10-267887 | | 10/1998 |
| JP | 11-344460 A | * | 12/1999 |
| WO | WO 00/50630 | | 8/2000 |
| WO | WO 01/71328 | | 9/2001 |

OTHER PUBLICATIONS

JPO English language computer translation of Miyashita et al. (JP 11-344460 A) Dec. 14, 1999.*
CAPLUS abstract (JP 04-264246 A) Yoshioka et al. Sep. 21, 1992.*
Chinese Office Action dated Jan. 26, 2007 (with English Translation).

* cited by examiner

*Primary Examiner*—Alex Noguerola
(74) *Attorney, Agent, or Firm*—McDermott Will & Emery LLP (57) ABSTRACT

A biosensor capable of measuring the concentration of one or more specific substances in one or more sample solutions almost simultaneously is provided. The biosensor comprises a plurality of sensor units, and each of the sensor units comprises an electrode system including a working electrode and a counter electrode on an insulating base plate and a reagent system including an oxidoreductase and an electron mediator. The biosensor is so configured that sample solutions supplied to the respective sensor units reach the respective reagent systems at different times. Specifically, each of the sensor units has a controlling system between a sample supply inlet and the reagent system, and the controlling system controls the time it takes for the sample solution to reach the reagent system from the sample supply inlet.

7 Claims, 10 Drawing Sheets

BIOSENSOR AND MEASURING METHOD USING THE SAME

BACKGROUND OF THE INVENTION

The present invention relates to a biosensor for measuring the concentration of one or more specific substances contained in one or more sample solutions and a measuring method using the biosensor.

As a conventional biosensor for measuring the concentrations of a plurality of specific substances simultaneously, there is a flow injection type biosensor. One such example is Flow Injection Analyzer (FIA) YSI MODEL 2700 SELECT (Yellow Spring Instrument Co., Inc.), which is a biosensor utilizing an immobilized enzyme membrane and electrode reaction, and its operation for simultaneously measuring glucose and L-lactic acid contained in a sample solution is described below. First, the tip end of a sample suction tube is immersed in a sample solution to suck the sample solution into a measuring system, whereby the sample solution is supplied into a sample chamber which is a measuring site. At the same time, a certain amount of buffer solution is also introduced into the sample chamber, where the sample solution and the buffer solution are stirred and mixed with each other by a stirrer of the sample chamber. The sample chamber is furnished with two electrodes having an immobilized enzyme membrane of glucose oxidase (hereinafter referred to as GOx) and an immobilized enzyme membrane of lactate oxidase (hereinafter referred to as LOD), respectively. After a lapse of a predetermined time period from the supply of the sample solution and the buffer solution, an electrochemical measurement is performed to calculate the concentrations of glucose and L-lactic acid contained in the sample solution.

Also, an example of the biosensor for measuring a single specific substance in a plurality of sample solutions successively is Glucoroder GTX (A&T Co., Inc.), which measures the concentration of glucose in blood, and its measuring operation is described below. A certain amount of plasma, which is a sample solution, is filled in the sample cups of a circular fraction collector, and the sample cups are set to the fraction collector to start a measurement. First, an aspirator automatically sucks a certain amount of the sample solution from the first sample cup on the fraction collector and moves to a measuring chamber containing a buffer solution, where the sample solution is diluted with the buffer solution by a predetermined dilution factor. Subsequently, an immobilized enzyme electrode with an immobilized GOx membrane is immersed in the sample solution in the measuring chamber, and after a lapse of a predetermined time period, an electrochemical measurement is performed. When the measurement of the first sample cup is completed, the fraction collector turns so that the second sample cup moves to the position of the first sample cup, and the sample solution of the second sample cup is measured. In this way, upon completion of the measurement of one sample cup, the fraction collector turns so that another sample cup moves to the position where the aspirator can operate, and measurements can be performed successively.

Meanwhile, as a system for measuring a plurality of specific substances in a sample solution without dilution or stirring with ease, the following biosensor has been proposed in Japanese Laid-Open Patent Publication No. Hei 5-196596. This biosensor has electrode systems on opposite sides of the insulating base plate, one on each side. On each of the electrode systems, a reaction layer having a different enzyme or different combination of enzymes is formed directly or indirectly. A method of measuring glucose and fructose in a sample solution using this biosensor is described below. First, an electrode system is formed by screen printing on each side of the insulating base plate. A reaction layer containing GOx is formed on the electrode system on one side of the base plate, while a reaction layer containing fructose dehydrogenase (hereinafter referred to as FDH) is formed on the electrode system on the other side of the base plate. Further, a cover member is joined to each side of the base plate to fabricate a sensor. The cover member forms a sample solution supply pathway, through which a sample solution is introduced into the electrode system, between itself and the base plate. The enzyme reaction time of GOx is shorter than that of FDH. Thus, by applying a voltage to the electrode systems after one minute and two minutes, respectively, from the simultaneous supply of the sample solution to the respective sample supply inlets of the sensor, and measuring the current five seconds later, the concentrations of glucose and fructose in the sample solution can be quantified.

The above-described conventional biosensors of flow injection type for measuring the concentrations of a plurality of specific substances simultaneously need a buffer solution serving as a carrier for making a measurement. In the above example, since the buffer solutions of GOx and LOD are the same, the two components can be measured simultaneously. However, if the appropriate pHs of the enzymes for the plurality of specific substances to be measured or the appropriate kinds of buffer solutions are different, simultaneous measurement is impossible. Also, the measuring system becomes large-scale, and the maintenance becomes complicated.

Also, the above-described conventional biosensor for measuring a single specific substance contained in a plurality of sample solutions needs a large-scale means, such as the fraction collector, for supplying samples successively. Further, since simultaneous measurement is not possible, the sample solutions evaporate with passage of time, which may result in a decreased measuring accuracy.

Further, the above-described biosensor having a plurality of electrode systems on the base plate is unable to divide the current of the plurality of electrode systems and detect the current of each electrode system in the case where there is no difference in enzyme reaction time among the enzymes and combination of enzymes contained in a plurality of reaction layers. Thus, when there is no difference in enzyme reaction time among the enzymes for a plurality of specific substances to be measured and when the specific substance to be measured is one, measurement is not possible.

In view of these problems, an object of the present invention is to provide a biosensor having a simple structure and capable of measuring the concentrations of a plurality of specific substances simultaneously even in the cases where the appropriate pHs of the enzymes for the plurality of specific substances to be measured or the appropriate kinds of buffer solutions are different and there is no difference in enzyme reaction time among the enzymes.

Another object of the present invention is to provide a biosensor having a simple structure and capable of measuring a single specific substance contained in a plurality of sample solutions continuously with high accuracy.

Further object of the present invention is to provide a measuring method using the biosensor.

BRIEF SUMMARY OF THE INVENTION

The present invention provides a biosensor comprising: a plurality of sensor units each comprising an electrode system including a working electrode and a counter electrode on an insulating base plate and a reagent system including an oxidoreductase and an electron mediator on or near the electrode system; a sample supply inlet provided for each of the sensor units or for every some sensor units; and a plurality of controlling systems for controlling the time it takes for a sample solution to reach the reagent system from the sample supply inlet, each controlling system being provided between the sample supply inlet and each of the reagent systems of the sensor units, wherein the respective controlling systems are different from one another so that the sample solution supplied to the sample supply inlet reaches the respective reagent systems of the sensor units at different times.

The biosensor of the present invention determines the concentration of a specific substance contained in a sample solution supplied to each of the sensor units in the following manner. When a sample solution supplied to the sensor unit dissolves the reagent system after a lapse of a time period determined by the controlling system, the specific substance in the sample solution reacts with the oxidoreductase of the reagent system to cause an electrochemical change of the electron mediator, and this electrochemical change is detected by measuring a response current when a voltage is applied between the working electrode and the counter electrode. This measuring principle is disclosed, for example, in U.S. Pat. No. 5,120,420, which is incorporated herein by reference in its entirety.

The biosensor of the present invention has the plurality of sensor units, and has different configurations depending on whether one sample supply inlet, from which a sample solution is supplied to the electrode system, is shared by the respective sensor units or is provided for each of the sensor units. Further, depending on whether a measuring electrode terminal and a counter electrode terminal are shared by the respective sensor units or are provided for each of the sensor units in order to detect electrochemical changes in the electrode systems of the sensor units, the biosensor also has different configurations in terms of electric circuit, and there are different measuring methods accordingly.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

A biosensor of the present invention comprises a plurality of sensor units, and each of the sensor units comprises: an electrode system including a working electrode and a counter electrode; a reagent system including an oxidoreductase and an electron mediator on or near the electrode system; and a controlling system for controlling the time it takes for a sample solution to reach the reagent system from a sample supply inlet. The sample supply inlet is provided for each of the sensor units or shared by the respective sensor units, and the controlling system is provided between the sample supply inlet and the reagent system. The biosensor is so configured that the respective controlling systems are different from one another so that the sample solution supplied to the sample supply inlet reaches the respective reagent systems of the sensor units at different times.

The reagent system is positioned such that at least part of the reagent system comes in contact with the sample solution supplied to the sensor unit. It is particularly preferable that the reagent system be provided on or near the electrode system. The reagent system may be provided in a state of being mixed with a conductive material constituting the working electrode or the counter electrode.

In a biosensor of a first preferable mode of the present invention, each of the senor units has a sample supply inlet, and the biosensor has one working electrode terminal connected in parallel to the respective working electrodes of the sensor units and one counter electrode terminal connected in parallel to the respective counter electrodes of the sensor units.

A method for determining the concentration of a specific substance contained in each of sample solutions supplied to an arbitrary number N of sensor units of this biosensor comprises the steps of: (a) supplying the sample solutions almost simultaneously to the respective sample supply inlets of the sensor units; (b) applying a voltage between the working electrode terminal and the counter electrode terminal and measuring a response current N times at intervals determined by the respective controlling systems of the sensor units; and (c) determining the concentration of the specific substance contained in each of the sample solutions supplied to the respective sensor units from the N measured values of the response current. In this case, the sample solutions supplied to the sensor units may be the same sample solution or different sample solutions.

In a biosensor of a second preferable mode of the present invention, each of the sensor units has a sample supply inlet, and each of the sensor units further has a working electrode terminal connected to the working electrode and a counter electrode terminal connected to the counter electrode.

A method for determining the concentration of a specific substance contained in each of sample solutions supplied to an arbitrary number N of sensor units of the second biosensor comprises the steps of: (a) supplying the sample solutions almost simultaneously to the respective sample supply inlets of the sensor units; (b) applying a voltage between the working electrode terminal and the counter electrode terminal and measuring a current response sequentially unit by unit, a total of N times, at intervals determined by the respective controlling systems of the sensor units; and (c) determining the concentration of the specific substance contained in each of the sample solutions supplied to the respective sensor units from the N measured values of the response current. The sample solutions supplied to the sensor units may be the same sample solution or different sample solutions.

In a biosensor of a third preferable mode of the present invention, the biosensor has one sample supply inlet shared by the respective sensor units, and the biosensor further has one working electrode terminal connected in parallel to the respective working electrodes of the sensor units and one counter electrode terminal connected in parallel to the respective counter electrodes of the sensor units.

A method for determining the concentration of a specific substance contained in a sample solution supplied to an arbitrary number N of sensor units of the third biosensor comprises the steps of: (a) supplying the sample solution to the sample supply inlet; (b) applying a voltage between the working electrode terminal and the counter electrode terminal and measuring a response current N times at intervals determined by the respective controlling systems of the sensor units; and (c) determining the concentration of the specific substance contained in the sample solution supplied to the respective sensor units from the N measured values of the response current. The sample solution supplied to the N sensor units may contain one or more specific substances, and the specific substances measured by the respective sensor units may be the same or different.

In a biosensor of a fourth preferable mode of the present invention, the biosensor has one sample supply inlet shared by the respective sensor units, and each of the sensor units has a working electrode terminal connected to the working electrode and a counter electrode terminal connected to the counter electrode.

A method for determining the concentration of a specific substance contained in a sample solution supplied to an arbitrary number N of sensor units of the fourth biosensor comprises the steps of: (a) supplying the sample solution to the sample supply inlet; (b) applying a voltage between the working electrode terminal and the counter electrode terminal and measuring a current response sequentially unit by unit, a total of N times, at intervals determined by the respective controlling systems of the sensor units; and (c) determining the concentration of the specific substance contained in the sample solution supplied to the respective sensor units from the N measured values of the response current. The sample solution supplied to the N sensor units may contain one or more specific substances, and the specific substances measured by the respective sensor units may be the same or different.

In the above-described measuring methods, it is preferable to measure the response current of the electrode system of a sensor unit after the working electrode and the counter electrode of the sensor unit come in contact with a sample solution to cause liquid junction. In other words, it is preferable to measure it after detecting the change in electric resistance between the electrodes. Since the liquid junction allows determination of the arrival of the sample solution at the electrode system, accurate measurement becomes possible.

A preferable controlling system which is used in the biosensor of the present invention comprises a layer comprising a hydrophilic polymer, and the respective controlling systems of the sensor units are different from one another in the speed with which the layer comprising a hydrophilic polymer dissolves in the sample solution.

Another preferable controlling system comprises a layer of a porous material or a fibrous substance having pores through which the sample solution passes, and the respective controlling systems of the sensor units are different from one another in the speed with which the sample solution passes through the layer of the porous material or the fibrous substance.

Still another preferable controlling system comprises a sample solution supply pathway which extends from the sample supply inlet to the reagent system, and the respective controlling systems are different from one another in the length of the sample solution supply pathway.

In the case of using the same hydrophilic polymer as the controlling system for each of the sensor units, the speed with which the layer comprising the hydrophilic polymer dissolves in the sample solution may be changed from unit to unit by adjusting the thickness, density or the like of the layer comprising the hydrophilic polymer. Also, the use of hydrophilic polymers having different solubilities allows the dissolution speeds to differ from unit to unit.

Examples of the hydrophilic polymer which may be used in the present invention include cellulose derivatives such as carboxymethyl cellulose, hydroxyethyl cellulose, hydroxypropyl cellulose, methyl cellulose, ethyl cellulose, and ethylhydroxyethyl cellulose, polyamino acid such as polylysine, polystyrene sulfonic acid, gelatin and its derivatives, polyacrylic acid and its salts, polymethacrylic acid and its salts, starch and its derivatives, a polymer of maleic anhydride or its salts, and agarose gel and its derivatives.

The speed with which the sample solution passes through the layer of the porous material or the fibrous substance having pores serving as the controlling system may be adjusted by the thickness, pore size, porosity or the like.

Examples of the porous material which may be used in the present invention include porous glass, porous ceramics, porous metal such as foamed metal and sintered metal, and activated carbon. Examples of the layer of a fibrous substance include non-woven fabric, glass fiber filter paper, and filter paper.

Embodiments of the present invention are specifically detailed below with reference to drawings. The structural drawings used herein are merely intended to facilitate understanding and are therefore not necessarily accurate in terms of the relative size and positional relation of the respective elements.

Embodiment 1

Figure 1:
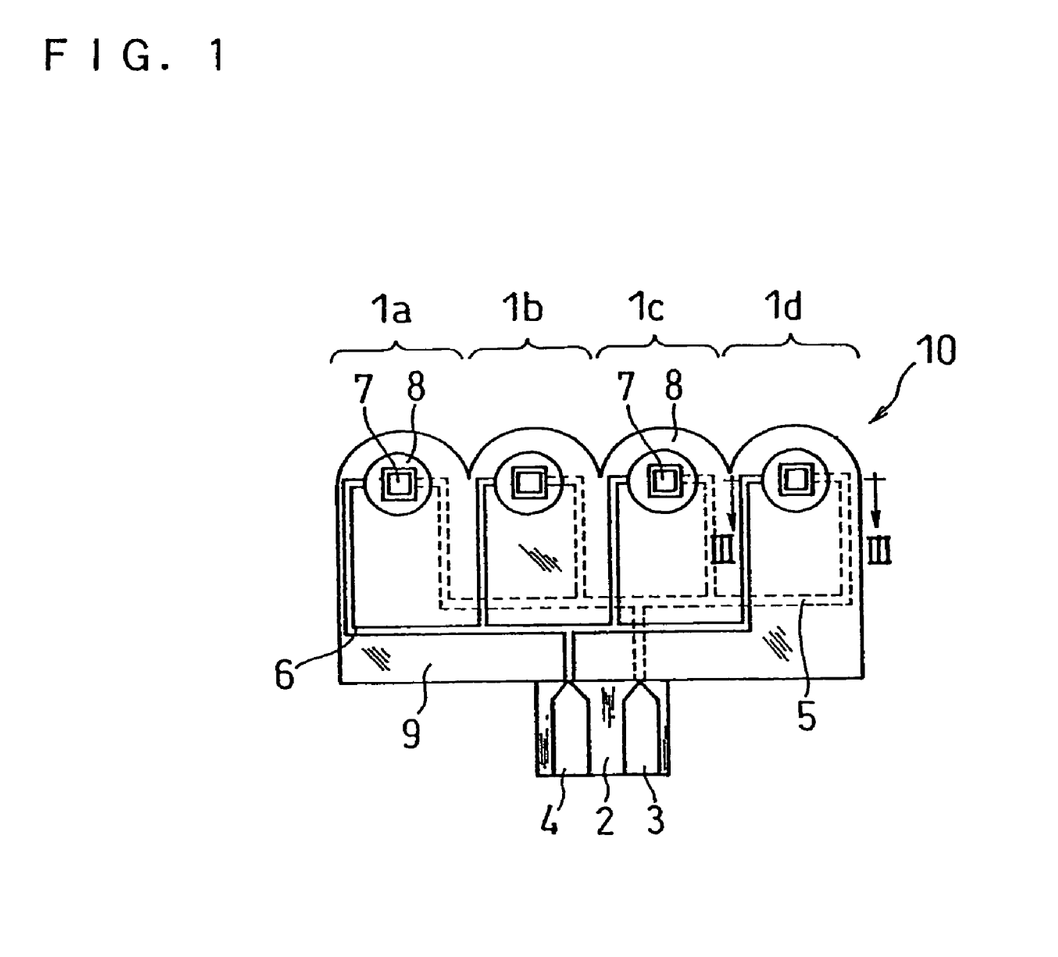
FIG. 1 is a plane view of a biosensor in one embodiment of the present invention from which the spacer and cover are omitted.
Figure 2:
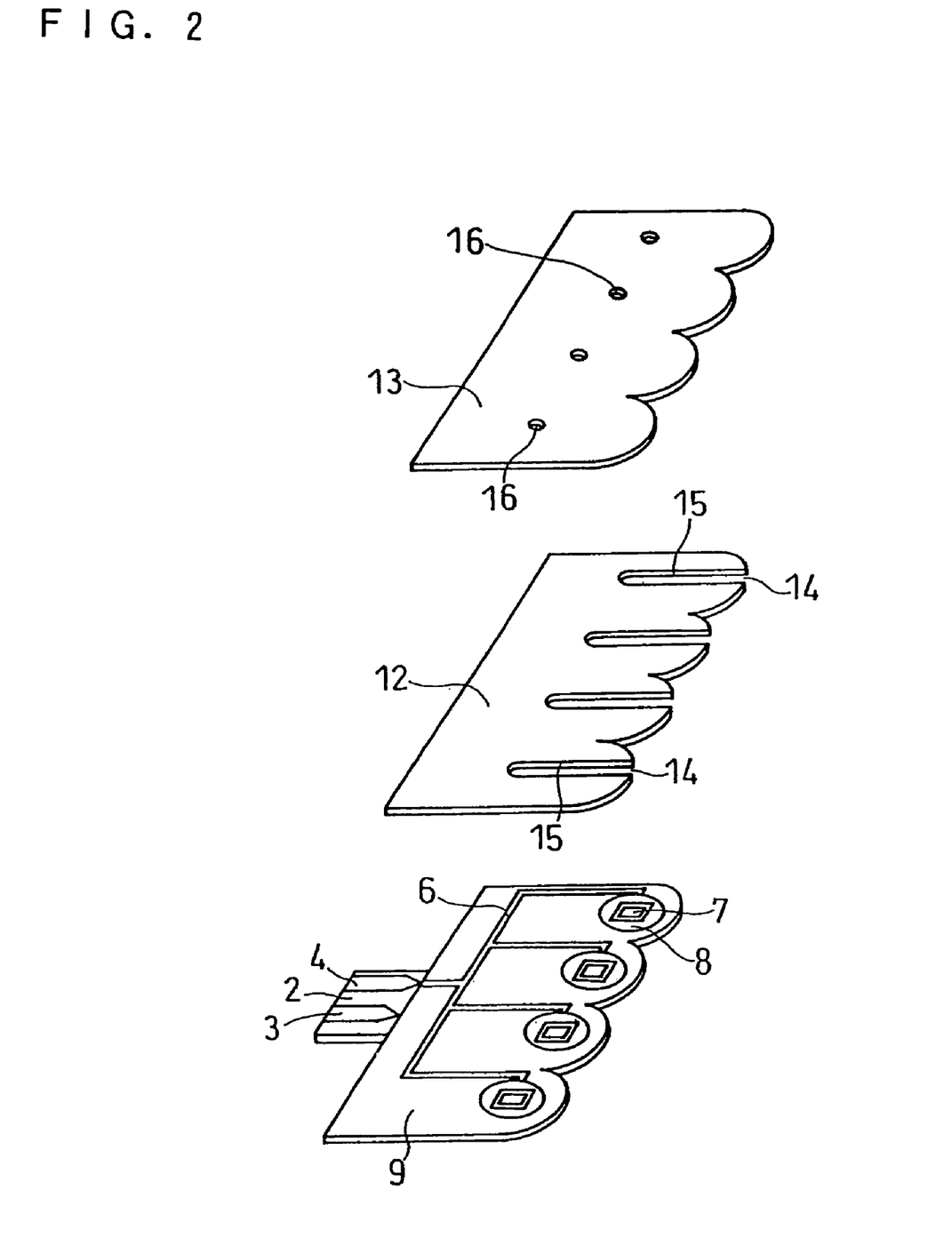
FIG. 2 is a decomposed perspective view of the biosensor of FIG. 1 from which the reagent system and controlling system are omitted.
Figure 3:
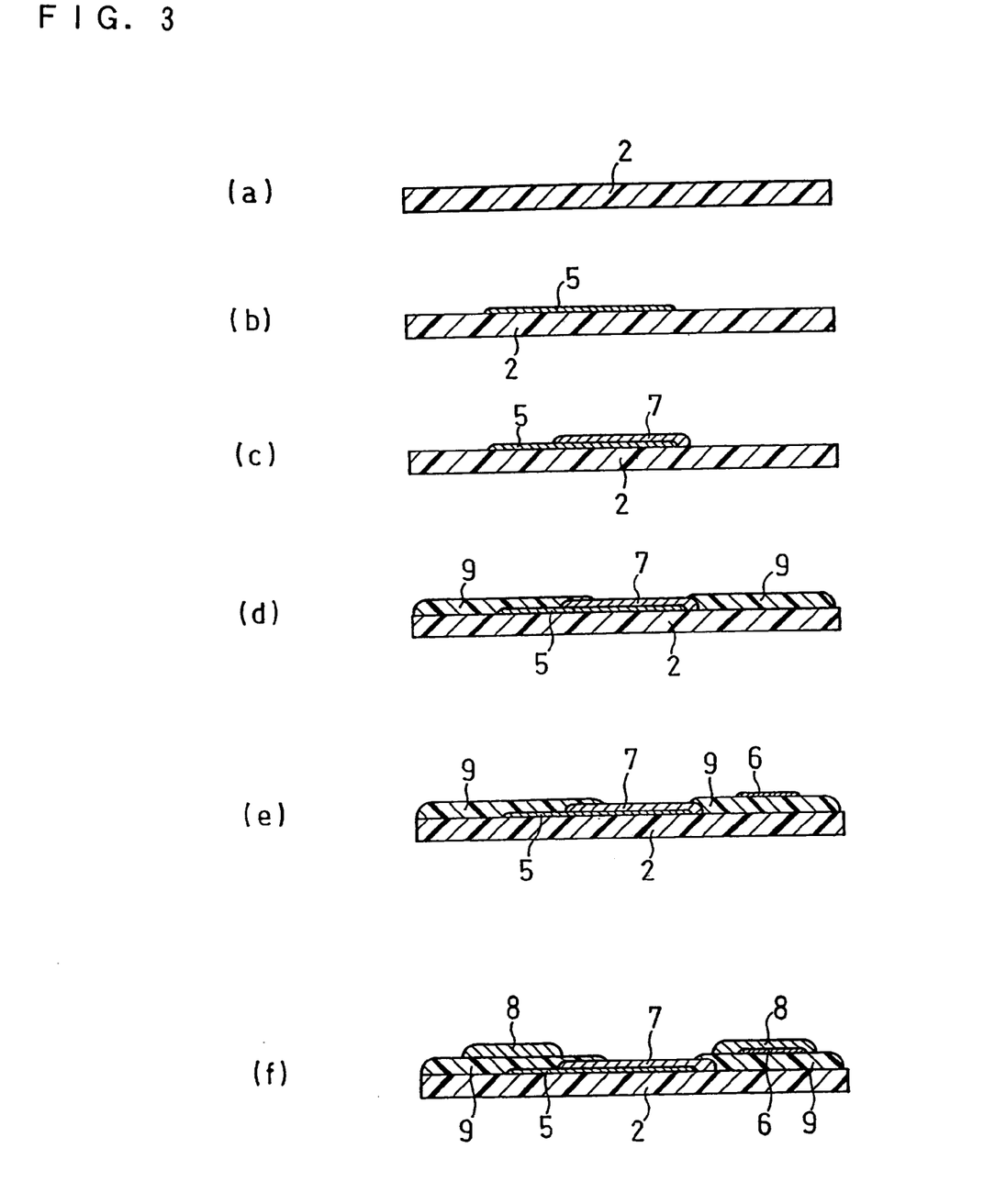
FIG. 3 is sectional views taken on line III—III of FIG. 1, showing processes of forming an electrode system.
Figure 4:
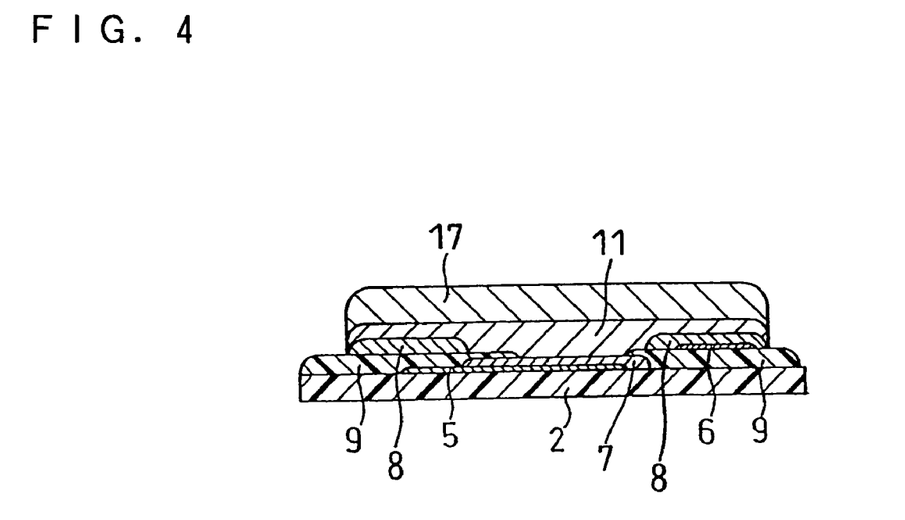
FIG. 4. is a sectional view of the biosensor with the reagent system and controlling system taken on line III—III of FIG. 1.

FIG. 1 is a plane view of a biosensor in Embodiment 1 from which the spacer and cover are omitted. FIG. 2 is a decomposed perspective view of the biosensor from which the reagent system and controlling system are omitted. FIG. 3 contains sectional views taken on line III—III of FIG. 1, showing processes of forming an electrode system. FIG. 4 is a sectional view of the biosensor with the reagent system and controlling system taken on line III—III of FIG. 1.

A biosensor 10 of this embodiment is produced as follows. First, a silver paste is printed on a base plate 2 made of an insulating resin by screen printing to form a working electrode terminal 3 and a working electrode lead 5 having 4 branches, as illustrated in FIG. 3 (b). Next, a conductive carbon paste containing a resin binder is printed to form 4 working electrodes 7, as illustrated in FIG. 3 (c). Subsequently, an insulating paste is printed to form an insulating layer 9, as illustrated in FIG. 3 (d). Further, a silver paste is printed to form a counter electrode terminal 4 and a counter electrode lead 6 having 4 branches, as illustrated in FIG. 3 (e). Lastly, a conductive carbon paste containing a resin binder is printed to form 4 counter electrodes 8, as illustrated in FIG. 3 (f). The insulating layer 9 regulates the area of the working electrodes 7 and insulates the working electrode lead 5 and the working electrodes 7 connected thereto from the counter electrode lead 6 and the counter electrodes 8 connected thereto.

Thereafter, a reagent system 11 including an enzyme and an electron mediator is formed over the electrode systems each consisting of the working electrode 7 and the counter electrode 8, and a controlling system 17 serving as a means for controlling the time it takes for a sample solution to reach the reagent system 11 is formed over the respective reagent systems 11. The controlling system 17 is, for example, a hydrophilic polymer layer, a porous material or a layer of a fibrous substance.

Lastly, a spacer 12 having slits 15 and a cover 13 having air vents 16 are bonded in succession to the base plate 2 to complete the biosensor 10. A sample solution supply pathway is formed in each of the slits 15 of the spacer 12, and the open end of each of the slits 15 serves as a sample supply inlet 14. When a sample solution is brought in contact with the sample supply inlet 14, the sample solution is introduced into the sample solution supply pathway by capillarity to reach the reagent system 11 through the controlling system 17.

In this way, the biosensor having four sensor units 1a, 1b, 1c and 1d is produced in this embodiment.

The principle on which the concentration of a specific substance in a sample solution is measured using this biosensor is explained below. The enzyme included in the reagent system 11 reacts with a substrate (specific substance) contained in a sample solution to reduce an oxidized form electron mediator. Upon application of a voltage between the electrodes with the working electrode being positive, a current oxidizing the reduced electron mediator flows through the electrodes, and this current is measured. The measured current value is proportional to the amount of the reduced electron mediator resulting from the reaction between the enzyme and the substrate, and the amount of the reduced electron mediator is proportional to the concentration of the substrate contained in the sample solution. Accordingly, the concentration of the substrate contained in the sample solution can be calculated from the obtained current value.

Next, the method of measuring the concentration of a specific substance in a plurality of sample solutions using the biosensor of this embodiment based on the above-described measuring principle is explained in detail. The controlling system 17 controls the time it takes for a sample solution to reach the reagent system 11 from the sample supply inlet 14. The respective controlling systems 17 of the sensor units are different from one another such that sample solutions simultaneously supplied to the sample supply inlets reach the respective reagent systems of the sensor units at different times. Therefore, when sample solutions are supplied substantially simultaneously to the respective sensor units of the biosensor, the sample solutions reach the respective reagent systems 11 of the sensor units at different times.

The measuring method using the biosensor of Embodiment 1 having an arbitrary number N of sensor units is specifically described below. Time measurement is started when sample solutions are simultaneously supplied to the respective sample supply inlets of the sensor units. One of the sample solutions reaches the reagent system of one of the sensor units (first sensor unit) fastest to cause a reaction at its electrode system. The current resulting from this reaction and flowing between the measuring terminals 3 and 4 at time $t_1$, is taken as $I_{t1}$. Since the sample solutions supplied to the other sensor units than the first sensor unit have not reached their reagent systems then, the current $I_{1(t1)}$ flowing through the electrode system of the first sensor unit at time $t_1$, is derived as follows:

$$I_1(_{t1})=I_{t1}$$

The calibration curb showing the relation between the substrate concentration and the current value in the first sensor unit at time $t_1$ is expressed by a function $\alpha_1(_{t1})(i)$ wherein i is a current value. Then, the concentration $C_1$ of the specific substance in the sample solution measured based on the reaction at the electrode system of the first sensor unit is derived as follows:

$$C_1=\alpha_{1(t1)}\{I_{1(t1)}\}$$

Next, another reaction takes place at the electrode system when another sample solution reaches the reagent system of the second sensor unit the second fastest. The current resulting from the reactions at the electrode systems of the first and second sensor units and flowing between the measuring terminals 3 and 4 at time $t_2$ is taken as $I_{t2}$. Since the sample solutions supplied to the third and subsequent sensor units have not reached their reagent systems then, it is only the electrode systems of the first and second sensor units that the current is flowing through at time $t_2$. By taking the current flowing through the electrode system of the first sensor unit at time $t_2$ as $I_{1(t2)}$ and the current flowing through the electrode system of the second sensor unit at time $t_2$ as $I_{2(t2)}$, the current $I_{t2}$ flowing through the whole biosensor is derived as follows:

$$I_{t2}=I_{1(t2)}+I_{2(t2)}$$

Meanwhile, the concentration $C_1$ at time $t_1$ has been already obtained, and the calibration curb showing the relation between the substrate concentration and the current value in the first sensor unit at time $t_2$ is expressed by a function $\alpha_{1(t2)}(i)$. Then, the concentration $C_1$ is derived as follows:

$$C_1 = \alpha_{1(t2)}\{I_{1(t2)}\}$$

Therefore, $$I_{1(t2)} = \alpha_{1(t2)}^{-1}(C_1),$$

and $$I_{2(t2)} = I_{t2} - I_{1(t2)} = I_{t2} - \alpha_{1(t2)}^{-1}(C_1)$$

Meanwhile, the calibration curb showing the relation between the substrate concentration and the current value in the second sensor unit at time $t_2$ is expressed by a function $\alpha_{2(t2)}(i)$. Then, the concentration $C_2$ is derived as follows:

$$C_2 = \alpha_{2(t2)}\{I_{t2} - \alpha_{1(t2)}^{-1}(C_1)\}$$

In this way, the sample solutions sequentially reach the reagent systems of the sensor units, and the current resulting from the reaction at the electrode system to which the sample solution has newly reached adds to the current flowing between the terminals 3 and 4. Accordingly, the substrate concentration $C_n$ obtained from the current resulting from the reaction at the electrode system of the Nth sensor unit can be expressed as follows:

$$C_n = \alpha_{n(tn)}\{I_{tn} - \{\alpha_{1(tn)}^{-1}(C_1) + \ldots + \alpha_{n-1(tn)}^{-1}(C_{n-1})\}$$

Since the biosensor of this embodiment comprises the plurality of sensor units each having the reagent system, the enzyme and buffer contained in the reagent system of each of the sensor units can be set appropriately depending on the substance to be measured. Thus, even in the case where the appropriate pHs of the enzymes for a plurality of specific substances to be measured or the appropriate kinds of buffers are different, the concentrations of the plurality of specific substances can be obtained by a series of operations of measuring the current flowing between the measuring terminals 3 and 4 at intervals over time. The biosensor of this embodiment is particularly effective when there is no difference in enzyme reaction time among the enzymes of the respective sensor units.

Also, the biosensor of this embodiment is so configured that the sample solutions are retained in the sample solution supply pathways. Thus, the measurement is not affected by the evaporation of the sample solutions although it takes different times for the sample solutions to reach the electrode systems. Therefore, it is possible to measure the concentration of a single specific substance contained in a plurality of sample solutions with high accuracy.

The biosensor of this embodiment needs only one pair of terminals for detecting the current resulting from the reactions at the electrode systems of the respective sensor units, so the number of sensor units can be increased or decreased freely. This makes it possible to freely change the kind of the specific substance and the number of samples to be measured by the series of operations. Also, since only one pair of terminals is used, only one pair of connectors is necessary for mounting the sensor onto a measuring device, so that it is possible to simplify the structure of the measuring device and downsize the measuring device.

Embodiment 2

Figure 5:
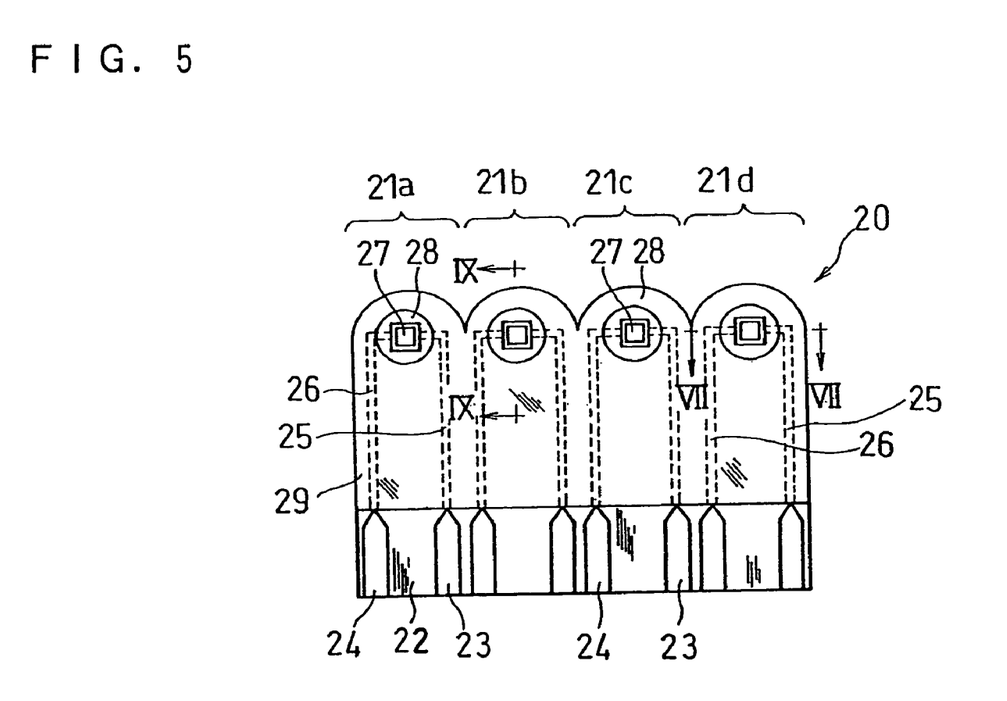
FIG. 5 is a plane view of a biosensor in another embodiment of the present invention from which the spacer and cover are omitted.
Figure 6:
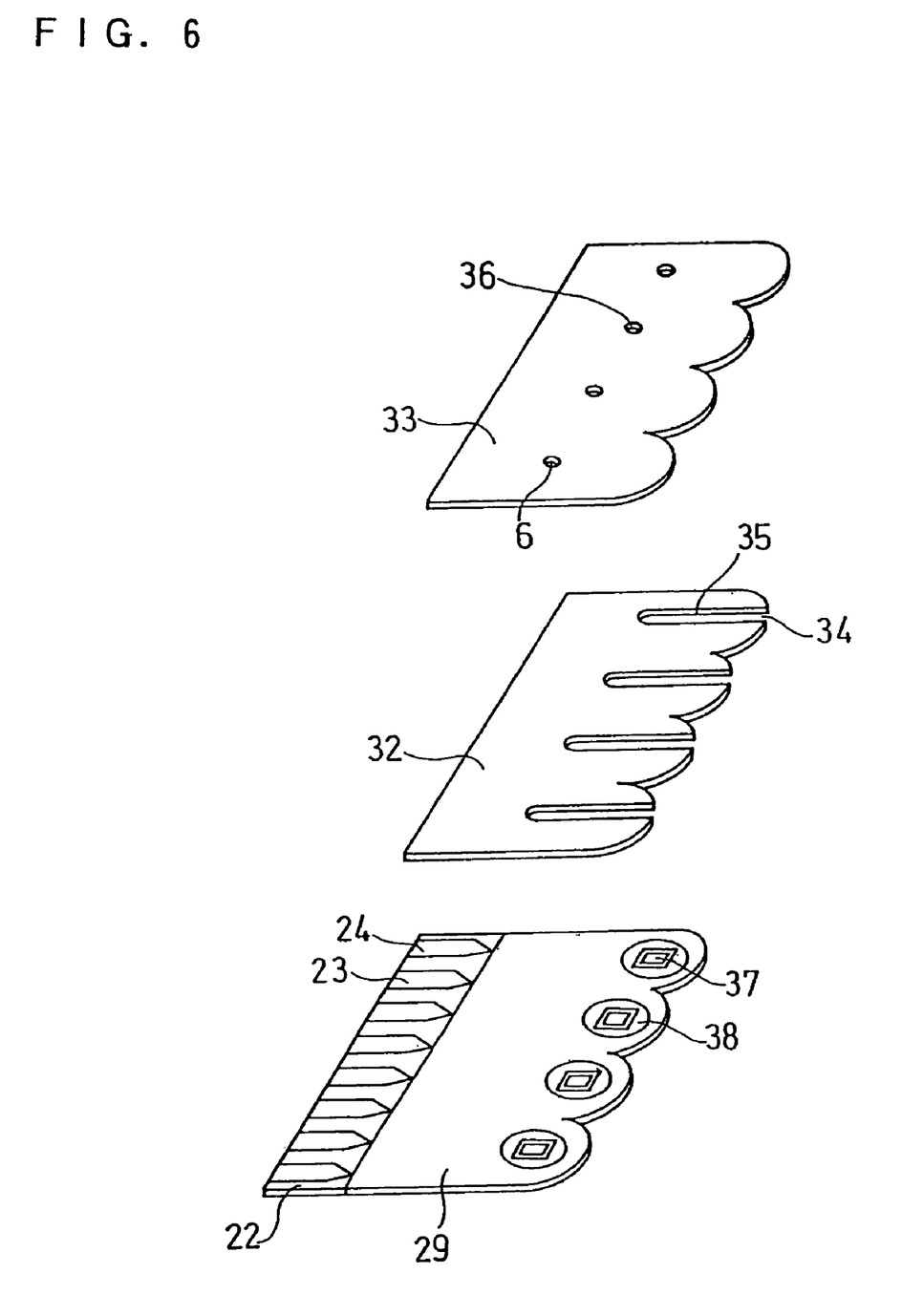
FIG. 6 is a decomposed perspective view of the biosensor of FIG. 5 from which the reagent system and controlling system are omitted.
Figure 7:
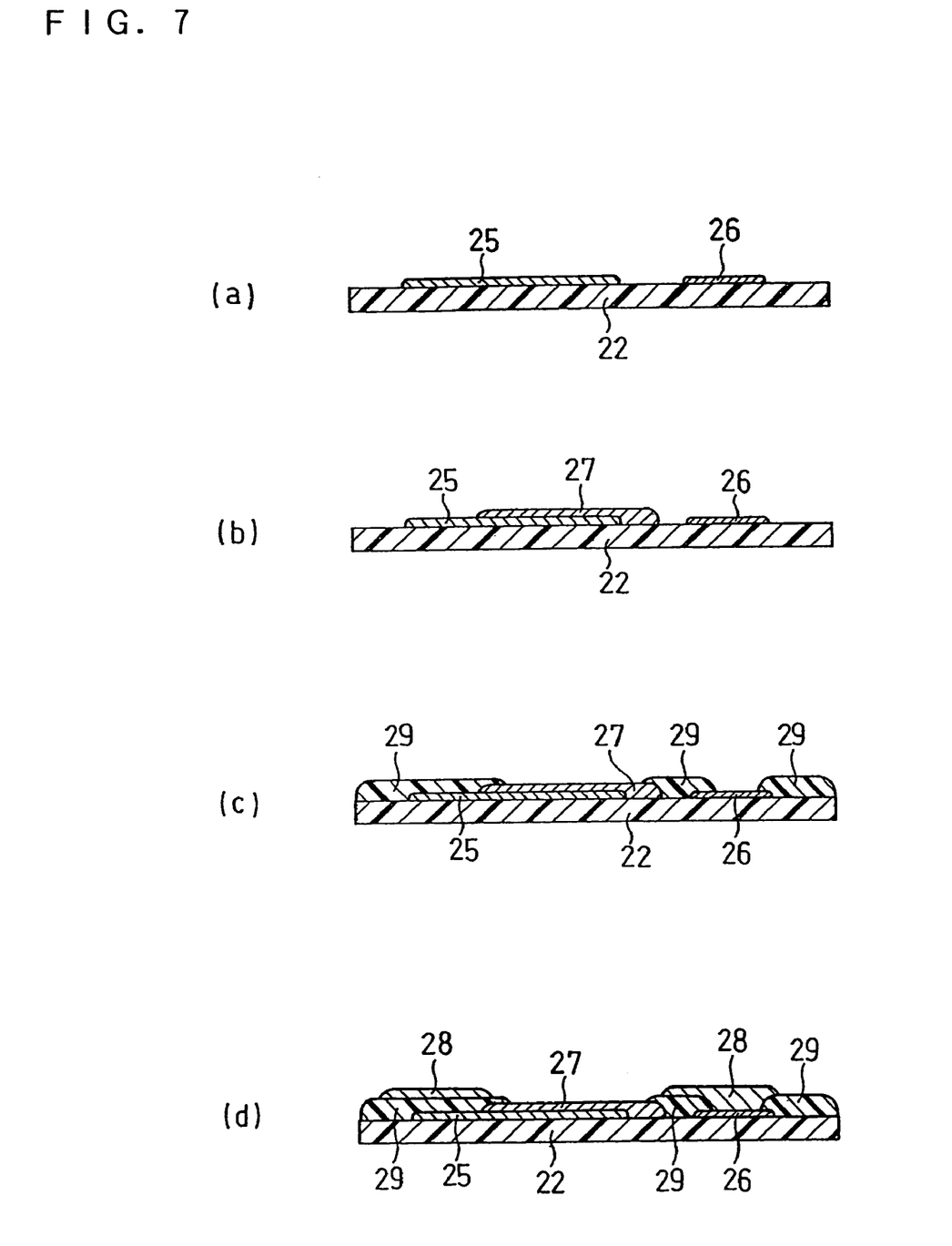
FIG. 7 is sectional views taken on line VII—VII of FIG. 5, showing processes of forming an electrode system.
Figure 8:
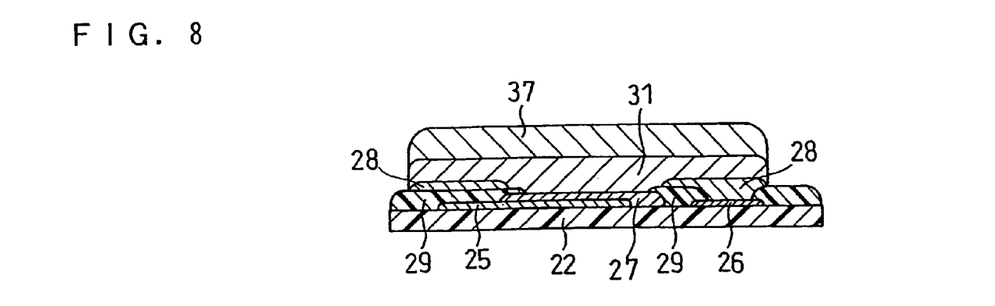
FIG. 8. is a sectional view of the biosensor with the reagent system and controlling system taken on line VII—VII of FIG. 5.

FIG. 5 is a plane view of a biosensor in Embodiment 2 from which the spacer and cover are omitted. FIG. 6 is a decomposed perspective view of the biosensor from which the reagent system and controlling system are omitted. FIG. 7 contains sectional views taken on line VII—VII of FIG. 5, showing processes of forming an electrode system. FIG. 8 is a sectional view of the biosensor with the reagent system and controlling system taken on line VII—VII of FIG. 5.

A biosensor 20 of this embodiment is produced as follows. First, a silver paste is printed on a base plate 22 made of an insulating resin by screen printing to form 4 working electrode terminals 23, 4 counter electrode terminals 24, 4 working electrode leads 25, and 4 counter electrode leads 26, as illustrated in FIG. 7 (*a*). Next, a conductive carbon paste containing a resin binder is printed to form 4 working electrodes 27, as illustrated in FIG. 7 (*b*). Subsequently, an insulating paste is printed to form an insulating layer 29, as illustrated in FIG. 7 (*c*). Lastly, a conductive carbon paste containing a resin binder is printed to form 4 counter electrodes 28, as illustrated in FIG. 7 (*d*).

Thereafter, a reagent system 31 including an enzyme and an electron mediator is formed over the respective electrode systems, and a controlling system 37 serving as a means for controlling the time it takes for a sample solution to reach the reagent system is formed over the respective reagent systems 31. The controlling system 37 is, for example, a hydrophilic polymer layer, a porous material or a layer of a fibrous substance.

Lastly, a spacer 32 having slits 35 and a cover 33 having air vents 36 are bonded in succession to the base plate 22 to complete the biosensor 20. A sample solution supply pathway is formed in each of the slits 35 of the spacer 32, and the open end of each of the slits 35 serves as a sample supply inlet 34. When a sample solution is brought in contact with the sample supply inlet 34, the sample solution is introduced into the sample solution supply pathway by capillarity to reach the reagent system 31.

Figure 9:
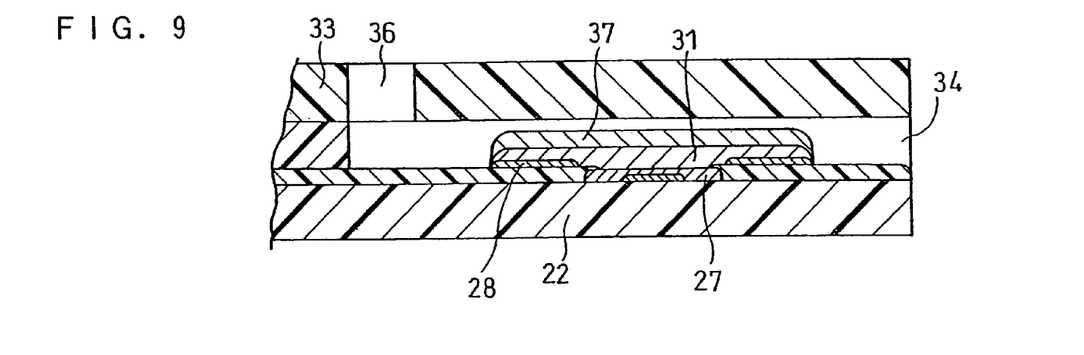
FIG. 9 is a sectional view taken on line IX—IX of FIG. 5.

FIG. 9 is a sectional view taken on line IX—IX of FIG. 5. The controlling system 37 is a hydrophilic polymer layer in this case. The sample solution supplied to the sample supply inlet 34 flows through the sample solution supply pathway formed in the slit 35 toward the air vent 36 by capillarity. When the sample solution dissolves the hydrophilic polymer layer of the controlling system, it then dissolves the reagent system 31 to initiate an enzyme reaction.

Figure 10:
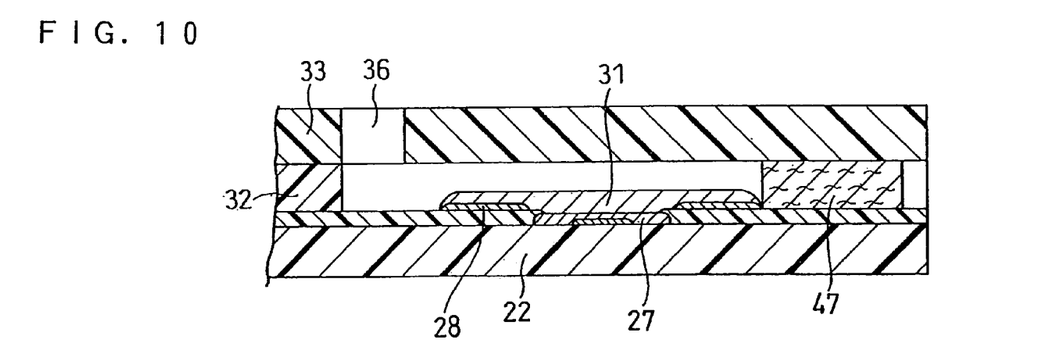
FIG. 10 is a sectional view of a sample solution supply pathway of a biosensor in another embodiment of the present invention.

FIG. 10 illustrates an example of a controlling system 47 being ceramics or a layer of a fibrous substance. In the sample solution supply pathway, the controlling system 47 is provided between the sample supply inlet and the reagent system 31, and a sample solution which has passed through the controlling system 47 reaches and dissolves the reagent system 31.

Figure 11:
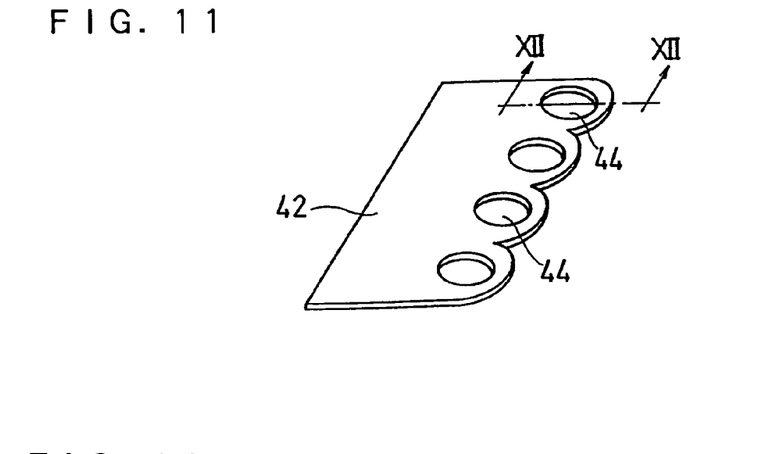
FIG. 11 is a perspective view of a cover of a biosensor in still another embodiment of the present invention.
Figure 12:
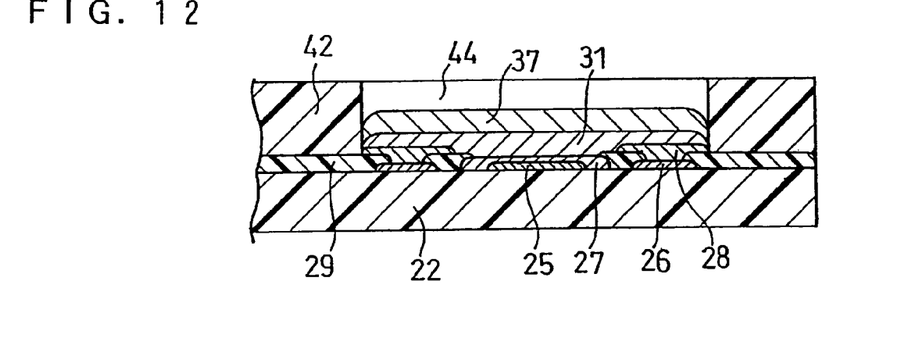
FIG. 12 is a sectional view taken on line XII—XII of FIG. 11.

FIG. 11 illustrates a cover 42 that is used instead of the spacer 32 and the cover 33 of FIG. 6. FIG. 12 is a sectional view of a biosensor using the cover 42 taken on line XII—XII of FIG. 11. The cover 42 has through holes 44 serving as sample supply inlets. A sample solution supplied to each of the through holes 44 comes in contact with the controlling system 37 and dissolves or permeates through the controlling system 37 to reach the reagent system 31.

It is needless to say that the structures as illustrated in FIGS. 9 to 12 are also applicable to Embodiment 1.

In this way, the biosensor having four sensor units 21*a*, 21*b*, 21*c* and 21*d* is produced in this embodiment.

The biosensor of this embodiment is different from that of Embodiment 1 in that each of the sensor units has terminals for measuring current, but its measuring principle of calculating the concentration of a substrate in a sample solution from the current flowing through the electrode system is the same as that of the biosensor of Embodiment 1. That is, a voltage is sequentially applied between the terminals of the electrodes of the sensor units unit by unit at intervals determined by the differences in structure of the respective controlling systems, and from the current values obtained upon the voltage applications, the concentration of the substrate contained in each of the sample solutions supplied to the respective sensor units can be calculated. Since the values measured by each of the sensor units are not affected by other sensor units, more accurate measurement becomes possible.

Embodiment 3

Figure 13:
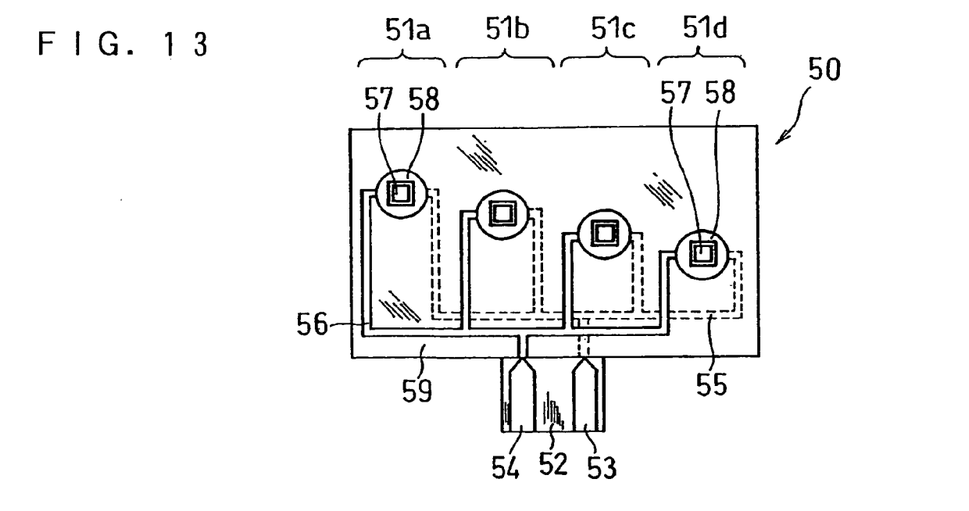
FIG. 13 is a plane view of a biosensor in still another embodiment of the present invention from which the spacer and cover are omitted.
Figure 14:
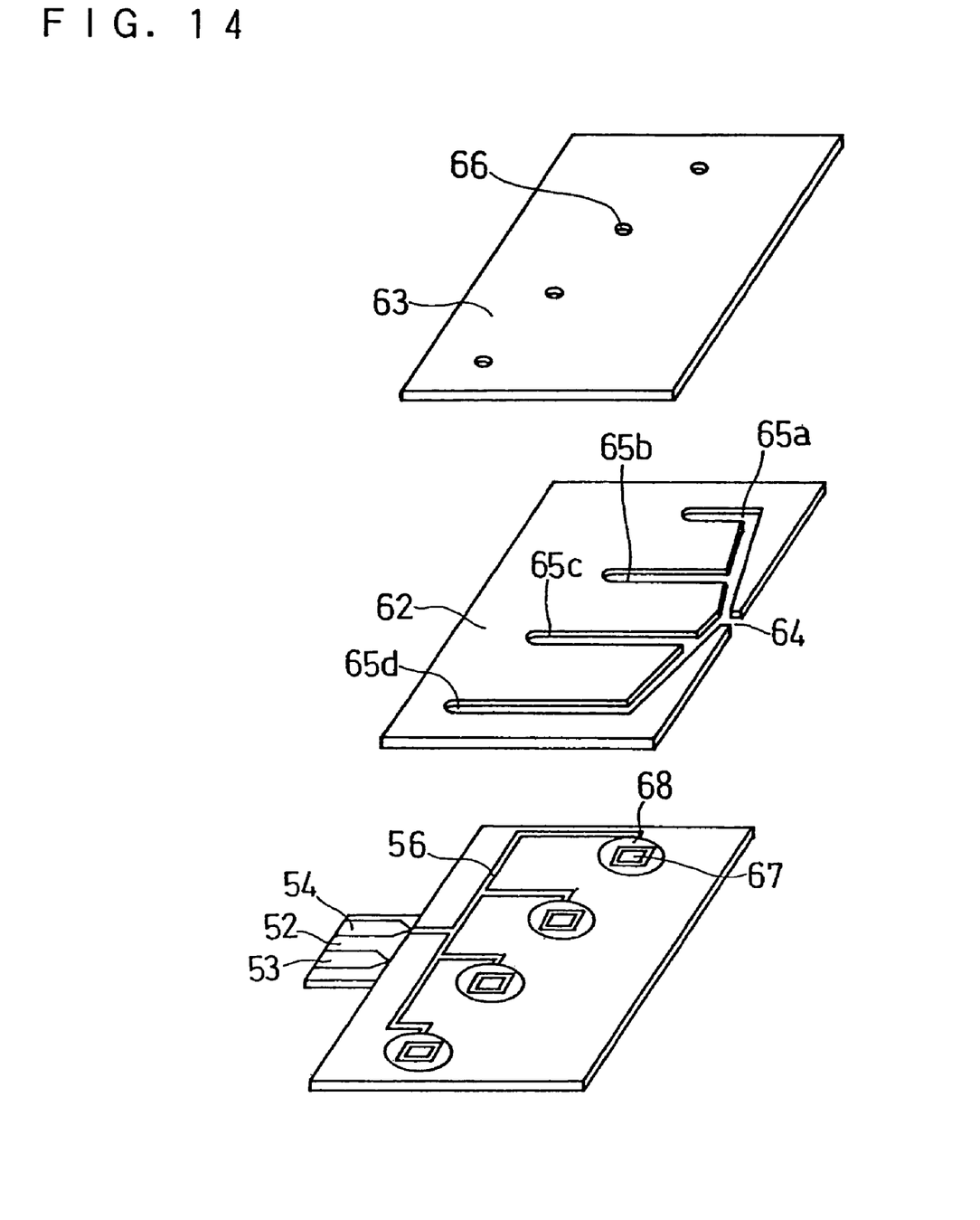
FIG. 14 is a decomposed perspective view of the biosensor of FIG. 13 from which the reagent system and controlling system are omitted.

FIG. 13 is a plane view of a biosensor in Embodiment 3 from which the spacer and cover are omitted. FIG. 14 is a decomposed perspective view of the biosensor from which the reagent system and controlling system are omitted.

A biosensor 50 of this embodiment is produced as follows. In the same manner as in Embodiment 1, a working electrode terminal 53, a working electrode lead 55 having 4 branches, 4 working electrodes 57, an insulating layer 59, a counter electrode terminal 54, a counter electrode lead having 4 branches 56, and 4 counter electrodes 58 are formed on a base plate 52. Subsequently, a reagent system is formed over the respective electrode systems. A spacer 62 of this embodiment has slits 65a, 65b, 65c, and 65d having different lengths for forming respective sample solution supply pathways of sensor units, and these slits communicate with one opening 64 which serves as a sample supply inlet. The spacer 62 and a cover 63 having four air vents 66 are bonded to the base plate 52 to complete the biosensor. The biosensor of this embodiment is so configured that a sample solution supplied to the one sample supply inlet is supplied to the respective sensor units through the different-length sample solution supply pathways. Because of the difference in length of the sample solution supply pathways, the sample solution supplied to the sample supply inlet reaches the respective reagent systems of the sensor units at different times. In the case where there is not sufficient difference in arrival time of the sample solutions at the reagent systems of the sensor units, the biosensor may further comprise a controlling systems as described in Embodiment 1 or 2. Although this embodiment uses a pair of terminals (a working electrode terminal and a counter electrode terminal) which is shared by the respective sensor units, a pair of terminals may be provided for each of the sensor units in the same manner as in Embodiment 2.

The biosensor of this embodiment is suited for measurement of different specific substances in a sample solution.

In Embodiments 1 and 2, one sample supply inlet was provided for each of the sensor units, but one sample supply inlet may be shared by the respective sensor units in the same manner as in Embodiment 3. In this case, the sample solution supply pathways extending from the one sample supply inlet to the respective reagent systems of the sensor units may have the same length or different lengths.

Figure 15:
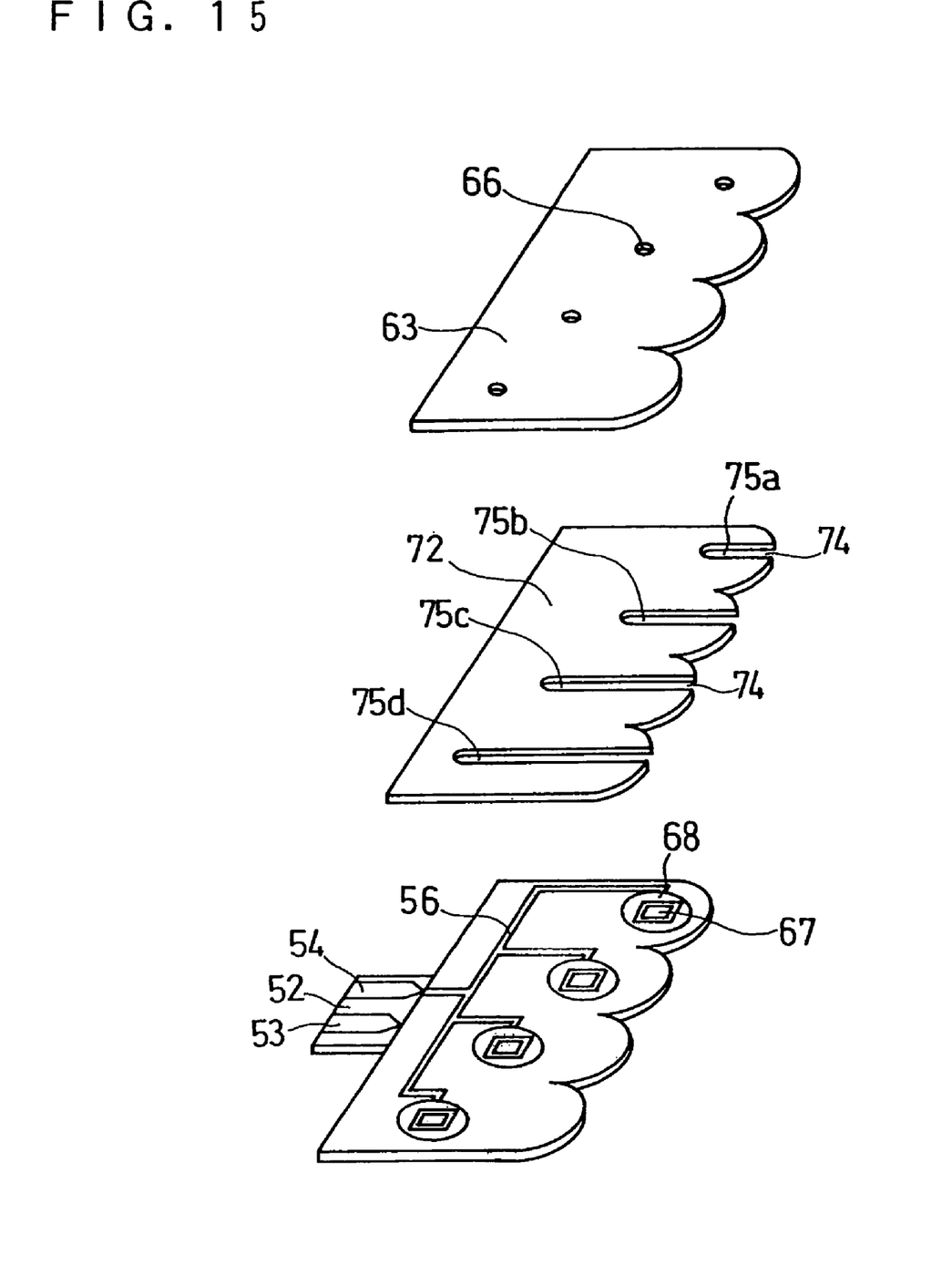
FIG. 15 is a decomposed perspective view of a biosensor in still another embodiment of the present invention from which the reagent system and controlling system are omitted.

In Embodiment 3, a pair of measuring terminals was used, but a pair of measuring terminals may be provided for each of the sensor units in the same manner as in Embodiment 2. In Embodiment 3, one sample supply inlet was shared by the respective sensor units, but one sample supply inlet may be provided for each of the sensor units as illustrated in FIG. 15. In FIG. 15, instead of the spacer 62 of FIG. 14 having one sample supply inlet, a spacer 72 having slits 75a, 75b, 75c and 75d of different lengths for forming sample solution supply pathways and 4 sample supply inlets 74 for the respective sensor units is used.

The measuring methods using the biosensors of the present invention are effective when a sample solution containing a plurality of substrates is supplied to the respective sensor units and the sensor units measure different substrates. These measuring methods are also effective when different sample solutions containing one or more substrates are supplied to the respective sensor units and the sensor units measure the same substrate or different substrates.

The present invention is more specifically detailed below by way of concrete examples.

EXAMPLE 1

A method of measuring glucose, fructose, L-lactic acid and alcohol contained in sample solutions using the biosensor of FIG. 1 is described. The reagent system 11 of each of the sensor units contains the following on the electrode system.

Sensor unit 1a for measuring glucose
   Enzyme: GOx
   Electron mediator: potassium ferricyanide
Sensor unit 1b for measuring fructose
   Enzyme: FDH
   Electron mediator: potassium ferricyanide
Sensor unit 1c for measuring L-lactic acid
   Enzyme: LOD
   Electron mediator: potassium ferricyanide
Sensor unit 1d for measuring alcohol
   Enzyme: alcohol dehydrogenase (ADH), diaphorase
   Coenzyme: β–nicotinamide adenin dinucleotide
   Electron mediator: potassium ferricyanide
   Ethanol solutions having polyvinyl pyrrolidone (hereinafter referred to as PVP) concentrations of 0, 0.5, 1.0, and 1.5% are dropped over the reagent systems 11 on the electrode systems of the sensor units 1a, 1b, 1c and 1d, respectively, and are dried to form PVP layers. The PVP layers serve as the controlling systems 17 for controlling the permeation of the sample solutions. The thicknesses of the respective PVP layers of the sensor units are different from one another. Due to this difference in PVP layer thickness, even when sample solutions are simultaneously supplied to the respective sensor units, the sample solutions reach the respective reagent systems 11 at intervals of approximately 30 seconds. That is, the sample solution supplied to the sensor unit 1a reaches the reagent system first, and the sample solutions supplied to the sensor units 1b, 1c and 1d sequentially reach the reagent systems with a time lag of approximately 30 seconds.

Sample solutions are supplied almost simultaneously to the respective sample supply inlets of the sensor units of the biosensor as described above. Since the sensor unit 1a for measuring glucose has no PVP layer over the reagent system, the sample solution which has reached the reagent system immediately dissolves the reagent system over the electrode system. Upon the dissolution, the working electrode 7 and the counter electrode 8 are electrically connected by liquid junction to cause a change in impedance between the electrodes. By this impedance change, the arrival of the sample solution at the electrode system is detected, and simultaneously with this detection, time measurement is started. After a lapse of 25 seconds, a voltage is applied between the electrodes with the working electrode being positive, and 5 seconds later, the current flowing between the electrodes is measured. From the current value measured, glucose concentration is calculated.

Almost simultaneously with the measurement of the current, the PVP layer of the sensor unit 1b for measuring fructose dissolves in the sample solution, followed by the dissolution of the reagent system 11. Fifty five seconds after the liquid junction of the electrode system of the sensor unit 1a, a voltage is applied between the electrodes of the sensor unit 1b, and 5 seconds later, the current is measured. The measured current value is the sum of the current value derived from the reaction of fructose and FDH and the current value derived from the reaction at the electrode system of the sensor unit 1a to which the sample solution has already reached. By subtracting the current value corresponding to the already obtained glucose concentration from this measured current value, the current value derived from the oxidation reaction of fructose can be obtained. Accordingly, fructose concentration can be calculated.

In this way, the concentrations of L-lactic acid and alcohol can also be obtained.

EXAMPLE 2

A method of simultaneously measuring glucose contained in four different sample solutions using the biosensor of FIG. 5 is described. The reagent system 31 containing the enzyme GOx and the electron mediator potassium ferricyanide is provided over the respective electrode systems of the sensor units. Subsequently, a glass fiber filter paper having a different thickness and a shape substantially the same as the electrode system is provided as the controlling system 37 over the respective reagent systems 31. When sample solutions are supplied to the respective sample supply inlets of the sensor units of the biosensor as described above, the sample solutions reach the reagent systems 31 of the sensor units at different times depending on the thickness of the glass fiber filter paper. By utilizing this difference in arrival time among the four sample solutions, a voltage is sequentially applied between the terminals of the respective sensor units at predetermined intervals, and the current which oxidizes the reduced electron mediator is measured. In this way, it is possible to calculate glucose concentrations in the four different sample solutions.

In Examples 1 and 2, PVP (hydrophilic polymer) and glass fiber filter paper (fibrous substance) were used as the means for controlling the time it takes for the sample solution to arrive at the reagent system 11 or 31. However, this is not to be construed as limiting the present invention.

As described above, even in the case where the appropriate pHs of the enzymes for a plurality of specific substances to be measured or the appropriate kinds of buffers are different, or in the case where there is no difference in reaction time among the enzymes, the present invention makes it possible to determine the concentrations of the plurality of specific substances by a series of operations with ease and high accuracy. The present invention also makes it possible to measure a single specific substance contained in a plurality of sample solutions in a continuous manner by a series of operations.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

The invention claimed is:

1. A biosensor comprising: a plurality of sensor units each comprising an electrode system including a working electrode and a counter electrode on an insulating base plate and a reagent system including an oxidoreductase and an electron mediator on or near the electrode system;
   a sample supply inlet provided for each of the sensor units or for every some sensor units; and a plurality of controlling systems for controlling the time it takes for a sample solution to reach the reagent system from the sample supply inlet, each controlling system being provided between the sample supply inlet and each of the reagent systems of the sensor units,
   wherein said respective controlling systems are different from one another so that the sample solution supplied to the sample supply inlet reaches the respective reagent systems of the sensor units at different times; and
   wherein said sample supply inlet is provided for each of the sensor units, and the biosensor has one working electrode terminal connected in parallel to the respective working electrodes of the sensor units and one counter electrode terminal connected in parallel to the respective counter electrodes of the sensor units.

2. A biosensor comprising: a plurality of sensor units each comprising an electrode system including a working electrode and a counter electrode on an insulating base plate and a reagent system including an oxidoreductase and an electron mediator on or near the electrode system;
   a sample supply inlet provided for each of the sensor units or for every some sensor units; and a plurality of controlling systems for controlling the time it takes for a sample solution to reach the reagent system from the sample supply inlet, each controlling system being provided between the sample supply inlet and each of the reagent systems of the sensor units,
   wherein said respective controlling systems are different from one another so that the sample solution supplied to the sample supply inlet reaches the respective reagent systems of the sensor units at different times; and
   wherein said sample supply inlet is provided for each of the sensor units, and each of the sensor units further has a working electrode terminal connected to the working electrode and a counter electrode terminal connected to the counter electrode.

3. A biosensor comprising: a plurality of sensor units each comprising an electrode system including a working electrode and a counter electrode on an insulating base plate and a reagent system including an oxidoreductase and an electron mediator on or near the electrode system;
   a sample supply inlet provided for each of the sensor units or for every some sensor units; and a plurality of controlling systems for controlling the time it takes for a sample solution to reach the reagent system from the sample supply inlet, each controlling system being provided between the sample supply inlet and each of the reagent systems of the sensor units,
   wherein said respective controlling systems are different from one another so that the sample solution supplied to the sample supply inlet reaches the respective reagent systems of the sensor units at different times; and
   wherein said controlling systems comprise a layer comprising a hydrophilic polymer, and said respective controlling systems of the senosr units are different from one another in the speed with which the layer comprising a hydrophilic polymer dissolves in the sample solution.

4. A biosensor comprising: a plurality of sensor units each comprising an electrode system including a working electrode and a counter electrode on an insulating base plate and a reagent system including an oxidoreductase and an electron mediator on or near the electrode system;
    a sample supply inlet provided for each of the sensor units or for every some sensor units; and a plurality of controlling systems for controlling the time it takes for a sample solution to reach the reagent system from the sample supply inlet, each controlling system being provided between the sample supply inlet and each of the reagent systems of the sensor units,
    wherein said respective controlling systems are different from one another so that the sample solution supplied to the sample supply inlet reaches the respective reagent systems of the sensor units at different times; and
    wherein said controlling systems comprise a layer of a porous material or a fibrous substance having pores through which the sample solution passes, and said respective controlling systems of the sensor units are different from one another in the speed with which the sample solution passes through the layer pf the porous material or the fibrous substance.

5. A method for determining the concentration of a specific substance contained in each of sample solutions supplied to an arbitrary number N of sensor units of the biosensor of claim 2,
    which detects an electrochemical change of the electron mediator caused by a reaction between the specific substance in the sample solution and the oxidoreductase of the reagent system upon dissolution of the reagent system into the supplied sample solution after a lapse of a time period determined by said controlling system, said electrochemical change being detected by measuring a response current when a voltage is applied between the working electrode and the counter electrode,
    said method comprising the steps of:
    (a) supplying the sample solutions almost simultaneously to the respective sample supply inlets of the sensor units;
    (b) applying a voltage between the working electrode terminal and the counter electrode terminal and measuring a response current N times at intervals determined by the respective controlling systems of the sensor units; and
    (c) determining the concentration of the specific substance contained in each of the sample solutions supplied to the respective sensor units from the N measured values of the response current,
    wherein the sample solutions supplied to the N sensor units are either the same sample solution or different sample solutions.

6. A method for determining the concentration of a specific substance contained in each of sample solutions supplied to an arbitrary number N of sensor units of the biosensor of claim 3,
    which detects an electrochemical change of the electron mediator caused by a reaction between the specific substance in the sample solution and the oxidoreductase of the reagent system upon dissolution of the reagent system into the supplied sample solution after a lapse of a time period determined by said controlling system, said electrochemical change being detected by measuring a response current when a voltage is applied between the working electrode and the counter electrode,
    said method comprising the steps of:
    (a) supplying the sample solutions almost simultaneously to the respective sample supply inlets of the sensor units;
    (b) applying a voltage between the working electrode terminal and the counter electrode terminal and measuring a current response sequentially unit by unit, a total of N times, at intervals determined by the respective controlling systems of the sensor units; and
    (c) determining the concentration of the specific substance contained in each of the sample solutions supplied to the respective sensor units from the N measured values of the response current,
    wherein the sample solutions supplied to the N sensor units are either the same sample solution or different sample solutions.

7. A method for determining the concentration of a specific substance contained in a sample solution supplied to an arbitrary number N of sensor units of a biosensor comprising:
    a plurality of sensor units each comprising an electrode system including a working electrode and a counter electrode on an insulating base plate and a reagent system including an oxidoreductase and an electron mediator on or near the electrode system;
    a sample supply inlet provided for each of the sensor units or for every some sensor units; and a plurality of controlling systems for controlling the time it takes for a sample solution to reach the reagent system from the sample supply inlet, each controlling system being provided between the sample supply inlet and each of the reagent systems of the sensor units,
    wherein said sample supply inlet is shared by the respective sensor units, and the biosensor further has one working electrode terminal connected in parallel to the respective working electrodes of the sensor units and one counter electrode terminal connected in parallel to the respective counter electrodes of the sensor units and;
    wherein said respective controlling systems are different from one another so that the sample solution supplied to the sample supply inlet reaches the respective reagent systems of the sensor units at different times
    wherein said sample supply inlet is shared by the respective sensor units, and the biosensor further has one working electrode terminal connected in parallel to the respective working electrodes of the sensor units and one counter electrode terminal connected in parallel to the respective counter electrodes of the sensor units;
    said method comprising the steps of:
    (a) supplying the sample solution to the sample supply inlet;
    (b) applying a voltage between the working electrode terminal and the counter electrode terminal and measuring a response current N times at intervals determined by the respective controlling systems of the sensor units; and
    (c) determining the concentration of the specific substance contained in the sample solution supplied to the respective sensor units from the N measured values of the response current,
    wherein the sample solution supplied to the N sensor units contains one or more specific substances, and the specific substances measured by the respective sensor units are the same or different.

\* \* \* \* \*

UNITED STATES PATENT AND TRADEMARK OFFICE
CERTIFICATE OF CORRECTION

| | |
|---|---|
| PATENT NO. | : 7,323,098 B2 |
| APPLICATION NO. | : 10/653257 |
| DATED | : January 29, 2008 |
| INVENTOR(S) | : Mariko Miyashita et al. |

It is certified that error appears in the above-identified patent and that said Letters Patent is hereby corrected as shown below:

In Column 16, Claim 7, after line 48 and before "said method comprising the steps of:" set forth on line 49, insert --which detects an electrochemical change of the electron mediator caused by a reaction between the specific substance in the sample solution and the oxidoreductase of the reagent system upon dissolution of the reagent system into the supplied sample solution after a lapse of a time period determined by said controlling system, said electrochemical change being detected by measuring a response current when a voltage is applied between the working electrode and the counter electrode,--.

Signed and Sealed this

Sixteenth Day of September, 2008

JON W. DUDAS
*Director of the United States Patent and Trademark Office*